United States Patent
Marcus (10) Patent No.: US 7,374,673 B2
(45) Date of Patent: May 20, 2008

(54) CHANNELED POLYMER FIBERS AS STATIONARY/SUPPORT PHASES FOR CHEMICAL SEPARATION BY LIQUID CHROMATOGRAPHY AND FOR WASTE STREAM CLEAN-UP

(75) Inventor: R. Kenneth Marcus, Seneca, SC (US)

(73) Assignee: Clemson University, Clemson, SC (US)

( * ) Notice: Subject to any disclaimer, the term of this patent is extended or adjusted under 35 U.S.C. 154(b) by 539 days.

(21) Appl. No.: 10/485,701

(22) PCT Filed: Aug. 13, 2002

(86) PCT No.: PCT/US02/25576

§ 371 (c)(1),
(2), (4) Date: Feb. 3, 2004

(87) PCT Pub. No.: WO03/022393

PCT Pub. Date: Mar. 20, 2003

(65) Prior Publication Data

US 2005/0023221 A1    Feb. 3, 2005

(51) Int. Cl.
*B01D 15/08* (2006.01)
(52) U.S. Cl. ............... 210/198.2; 210/321.87; 210/500.23; 210/502.1; 210/635; 210/638; 210/656
(58) Field of Classification Search .......... 210/321.78, 210/321.79, 321.8, 500.23, 638, 635, 656, 210/198.2, 321.87, 502.1
See application file for complete search history.

(56) References Cited

U.S. PATENT DOCUMENTS

| | | | |
|---|---|---|---|
| 4,111,815 A * | 9/1978 | Walker et al. .............. 210/487 |
| 4,187,333 A * | 2/1980 | Rembaum et al. .......... 427/230 |
| 4,657,742 A | 4/1987 | Beaver |
| 4,957,620 A | 9/1990 | Cussler |
| 5,160,627 A | 11/1992 | Cussler et al. |
| 5,234,594 A * | 8/1993 | Tonucci et al. ........ 210/500.26 |
| 5,277,821 A * | 1/1994 | Coughlin et al. ........... 210/644 |
| 5,604,012 A * | 2/1997 | Okamoto et al. .......... 428/136 |
| 5,855,798 A * | 1/1999 | Phillips et al. .............. 210/767 |
| 5,961,678 A * | 10/1999 | Pruette et al. ................ 55/485 |
| 5,972,505 A | 10/1999 | Phillips et al. |
| 6,270,674 B1 * | 8/2001 | Baurmeister et al. ....... 210/649 |
| 6,656,360 B2 * | 12/2003 | Rohrbach et al. ........... 210/638 |

* cited by examiner

*Primary Examiner*—Ernest G. Therkorn
(74) *Attorney, Agent, or Firm*—Dority & Manning, P.A.

(57) ABSTRACT

Polymer fibers having a novel cross-sectional geometry are used as stationary phase materials for liquid chromatography separations. Fibers of 20 to 50 micrometer diameters have surface-channel structures extending their entire lengths. Bundles of fibers having this novel cross-sectional geometry are packed in columns. Different polymer compositions permit the "chemical tuning" of the separation process. Channeled fibers composed of polystyrene and polypropylene have been used to separate mixtures of polyaromatic hydrocarbons (PAHs), Pb-containing compounds and fatty acids. Use of channeled fibers allows a wide range of liquid flow rates with very low backing pressures. Applications in HPLC, cap-LC, prep-scale separations, analytical separations, single fiber separations, waste remediation/immobilization, extraction of selected organic molecules/ions from solution, purification of liquid streams (process waste, drinking water, pure solvents), selective extraction of cell matter and bacteria from growth media, and immobilization of cell matter and bacteria are envisioned.

11 Claims, 11 Drawing Sheets

CHANNELED POLYMER FIBERS AS STATIONARY/SUPPORT PHASES FOR CHEMICAL SEPARATION BY LIQUID CHROMATOGRAPHY AND FOR WASTE STREAM CLEAN-UP

REFERENCE TO RELATED APPLICATIONS

This application is a 371 of PCT/US02/25576 filed Aug. 13, 2002.

BACKGROUND OF THE INVENTION

The present invention relates to chemical analysis and cleansing of liquid streams and more particularly to liquid chromatography and wastewater treatment.

At present, liquid-phase chemical separations are usually performed in "columns" prepared by the packing of metal tubes with spherical beads that are composed of either silica or polystyrene and have diameters of 10 to 50 μm. The more or less inert beads provide solid supports that are chemically modified to produce a surface having targeted chemical characteristics. For example, in performing reverse-phase liquid chromatography, long carbon chains (C-18) are affixed to the surfaces of the beads to produce a hydrophobic surface for the separation of non-polar organics.

Effective separations require dense packing of the beads into these columns to avoid dead-volume, which is any location within the column where turbulence can occur and interactions between molecules in the liquid and the surfaces of the beads are absent. As a consequence of dense packing, high driving pressures (2,000 to 10,000 psi) are required to overcome the backing pressures that otherwise would prevent the liquid phase from moving through the densely packed columns.

Alternatively, highly porous "monoliths" are formed within the columns to generate high surface areas for interaction with the species that flow through the columns. Here, the high backing pressures and a limited set of stationary phase chemistries can be restrictive. In the case of so-called "prep-scale" separations, the capital costs associated with producing large volume columns and the demands on the system hydraulics (i.e. pumps) are very high.

OBJECTS AND SUMMARY OF THE INVENTION

It is a principal object of the present invention to employ polymer fibers having channels extending axially along their surfaces, wherein the fibers are used as stationary phases in analytical separations of mixtures carried in liquid media and wherein the separation is based on chemical interactions, i.e., chromatography.

It is another principal object of the present invention to employ polymer fibers having channels extending axially along their surfaces, wherein the fibers are used as stationary phases in prep-scale separations of mixtures carried in liquid media and wherein the separation is based on chemical interactions, i.e., chromatography.

It is still another principal object of the present invention to employ polymer fibers having channels extending axially along their surfaces, wherein the fibers are used as stationary phases to selectively remove different chemical species from liquid wastewater treatment facilities.

It is a further principal object of the present invention to employ a single surface-channeled polymer fiber as a stationary phase to perform separations of at least one specie.

It is yet an additional principal object of the present invention to employ polymer fibers having channels extending axially along their surfaces, wherein the fibers are used as stationary phases in the process of performing micro-scale separations.

It is yet another principal object of the present invention to employ polymer fibers having channels extending axially along their surfaces, wherein the fibers are used as stationary phases to selectively extract cell matter and bacteria from growth media.

It is yet a further principal object of the present invention to employ polymer fibers having channels extending axially along their surfaces, wherein the fibers are used as stationary phases to selectively immobilize cell matter and bacteria.

It is a still further principal object of the present invention to employ polymer fibers having channels extending axially along their surfaces, wherein the fibers are used as stationary phases to extract selective organic molecules/ions from solution.

It is an additional principal object of the present invention to employ polymer fibers having channels extending axially along their surfaces, wherein the fibers are used as stationary phases in the purification of liquid streams (process waste, drinking water, pure solvents).

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, polymer fibers having a novel cross-sectional geometry are used as stationary phase materials for liquid chromatography separations. The novel cross-sectional geometry arises because each polymer fiber has channels extending axially and continuously along its surface over the entire length of the fiber. Each fiber desirably has a uniform nominal diameter (measured at the largest cross-sectional point-to-point location) in the range of 20 to 50 micrometers. A single one of these fibers can be used in single fiber separations. However, bundles of fibers having this novel cross-sectional geometry are packed into columns as stationary phase materials. Different polymer compositions permit the "chemical tuning" of the separation process. Channeled fibers composed of polystyrene and polypropylene have been used to separate mixtures of polyaromatic hydrocarbons (PAHs), Pb-containing compounds and lipids. Use of these so-called surface-channeled fibers allows a wide range of liquid flow rates with very low backing pressures.

The use of polymer fibers rather than beads is totally unique. The surface-channeled fibers provide very efficient solution mass transfer, but with very reactive surface areas. Column structures could take many forms, including the use of a single fiber in-laid in a micro-machined device.

Presently contemplated specific applications include use of surface-channeled polymer fibers in stationary phases in: analytical separations such as liquid chromatography (HPLC, cap-LC); prep-scale separations of specialty chemicals; micro-scale separations; single fiber separations; waste remediation/immobilization; extraction of selected organic molecules/ions from solution; purification of liquid streams (process waste, drinking water, pure solvents); selective extraction of cell matter and bacteria from growth media; and immobilization of cell matter and bacteria.

Potential markets for the invention would include analytical instrumentation; specialty chemicals; and pharmaceutical companies. Demand for the product would be based on its advantages in attaining throughput and productivity.

The accompanying drawings, which are incorporated in and constitute a part of this specification, illustrate one embodiment of the invention and, together with the description, serve to explain the principles of the invention.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

Figure 1:
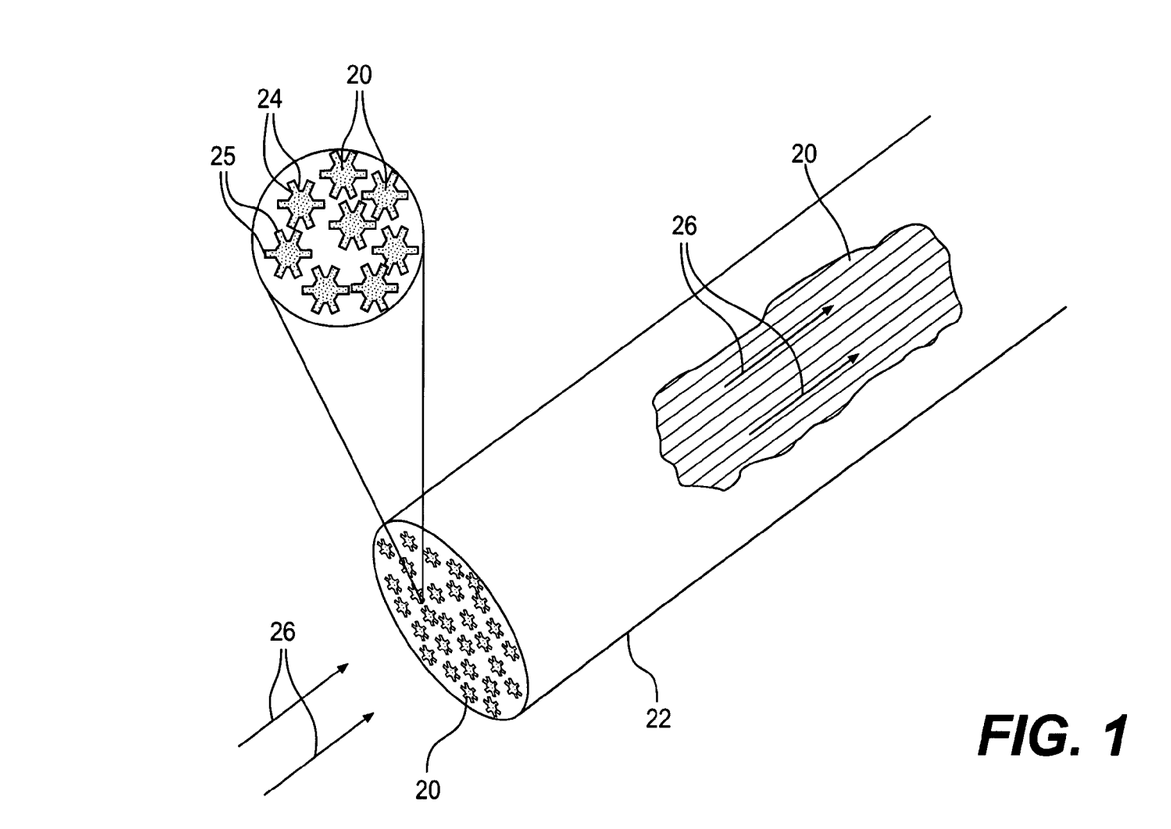
FIG. 1 is a cross-sectional representation of the liquid analyte flowing through channeled fibers placed in a single column formed by a 0.25 inch diameter stainless steel tube and including an expanded view window showing the end-on shape of the fibers and the potential irregular packing of the fibers in the column.

As shown in FIG. 1, bundles of surface-channeled polymer fibers 20 are packed into a column 22 that is formed desirably by a stainless steel tube having a uniform circular inside diameter of 0.25 inches and a length of 12 inches. The dimensions of the column 22 can be any size that is used in the practice of chromatography. Desirably, the length of each fiber 20 is substantially the same as the length of the column 22 and is disposed to extend within the column 22 over substantially the entire length of the column 22. However, fibers 20 that have lengths that are shorter than the length of the column 22 may be used, but are not preferred.

As shown schematically in cross-section in the expanded view window of FIG. 1, each fiber strand 20 has six co-linear channels 24 extending the entire length of the exterior surface of the fiber 20. Each channel 24 is defined by a pair of opposed walls 25 that extend generally and longitudinally and form part of the exterior surface of the fiber 20. Desirably, these channels 24 and walls 25 extend down the entire length of the fiber 20 parallel to the longitudinal axis of the fiber 20 and are co-linear on each fiber 20. This produces de facto substantially the same co-linear channels 24 along the entire length of the column 22.

In an alternative embodiment, the channels 24 can be configured to wrap around the length of the fiber 20 in a helical fashion. However, substantially all of the channels 24 must be co-linear on each fiber 20, and substantially all of the channels 24 of the fibers 20 within each column 22 follow a helix pattern that has the same pitch. The pitch is the number of complete turns of the channel 24 around the circumference of the fiber 20 per unit of length of the fiber 20. This also produces de facto substantially the same co-linear channels 24 along the entire length of the column 22.

Additionally, in the course of packing the fibers 20 into a bundle that lays along the entire length of the column 22, whether the individual fibers have purely linear channels 24 or helical ones, it is possible that one or more, even all, of the fibers 20 in the bundle will rotate about its/their own axis or the axis of the column 22 over the entire length of the column. In other words, the surface-channeled fibers 20 may twist as they lay from one end of the column 22 to the opposite end. Accordingly, the channels 24 and walls 25 also may twist somewhat.

In some embodiments of the present invention, a device can be provided to move fluid through the column 22 and thus through the channels 24 of the fibers 20. A pump (not shown) is typically provided for this purpose. The flow of liquid through the column 22 is schematically indicated by the arrows designated by the numeral 26 in FIG. 1. A portion of the column 22 is cut away in the view shown in FIG. 1 for the purpose of illustrating the flow of liquid 26 through the column 22 along the fibers 20 arranged with their longitudinal axes parallel to the longitudinal axis of the column 22. The nominal diameter of each fiber 20 desirably ranges 20 to 50 micrometers.

However, in some applications, the movement of the fluid may be effected without a device that is separate from the fibers themselves. In such embodiments, the fluid moves through the channels 24 of the fibers 20 solely by capillary action of the channels 24 of the fibers 20.

Advantageous in the use of these channeled polymer fibers 20 as stationary phase materials is their very high surface area-to-volume ratios. The number of channels 24 may vary from the six that are shown schematically in FIG. 1. The shape and the number of channels 24 should be dependent on achieving the desired attribute of very high surface area-to-volume ratios. In this regard, the helical channels 24 pack more surface area than the linear channels 24.

Another advantage of using these types of channeled polymer fibers 20 for this purpose is the fact that they generate very low backing pressures (500 to 800 psi for linear channels 24) for normal chromatography flow rates (0.5 to 3 mL/min). The lower backing pressure produced in the column 22 containing channeled polymer fibers 20 relative to the backing pressure produced in the conventional column containing beads, is believed to be due to the parallel-running channels 24. The ability to use fibers 20 of any desired length, while encountering relatively low backing pressures, would suggest great potential for using columns 22 of these channeled polymer fibers 20 in prep-scale separations or for waste remediation in a variety of industries.

There are different fabrication approaches to form channeled polymer fibers 20 of the sort demonstrated here. The process used to make these channeled, polymer fibers 20 is amenable to any polymers that can be spin-melted. For example, channeled fibers 20 may be melt spun from any of a number of different polymer precursors, including polypropylene precursors, polyester precursors, polyaniline precursors and precursors composed of polylactic acid. In general use, these channeled polymer fibers 20 tend to have a very strong wicking action for a variety of liquids, including water.

The ability to perform chemical separation of otherwise similar compounds for mixtures of polyaromatic hydrocarbons (PAHs), lipids, and organic and inorganic lead compounds has been demonstrated. This capability is particularly surprising given these seemingly chemically benign polymer compositions.

Figure 2A:
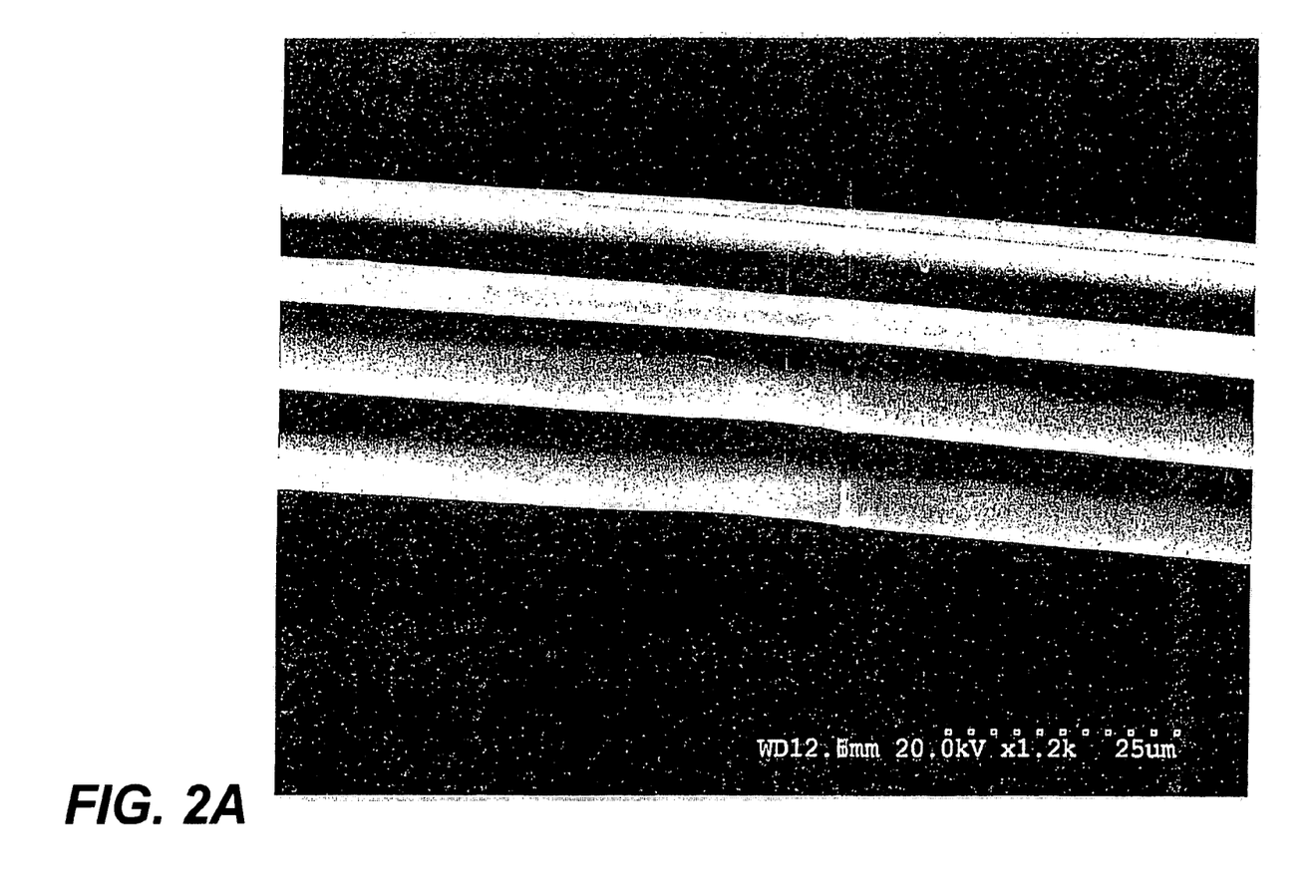
FIG. 2A is a photograph of an enlarged side plan view of an intermediate portion of a presently preferred embodiment of a channeled polyester fiber to be used in the column of the chromatograph.
Figure 2B:
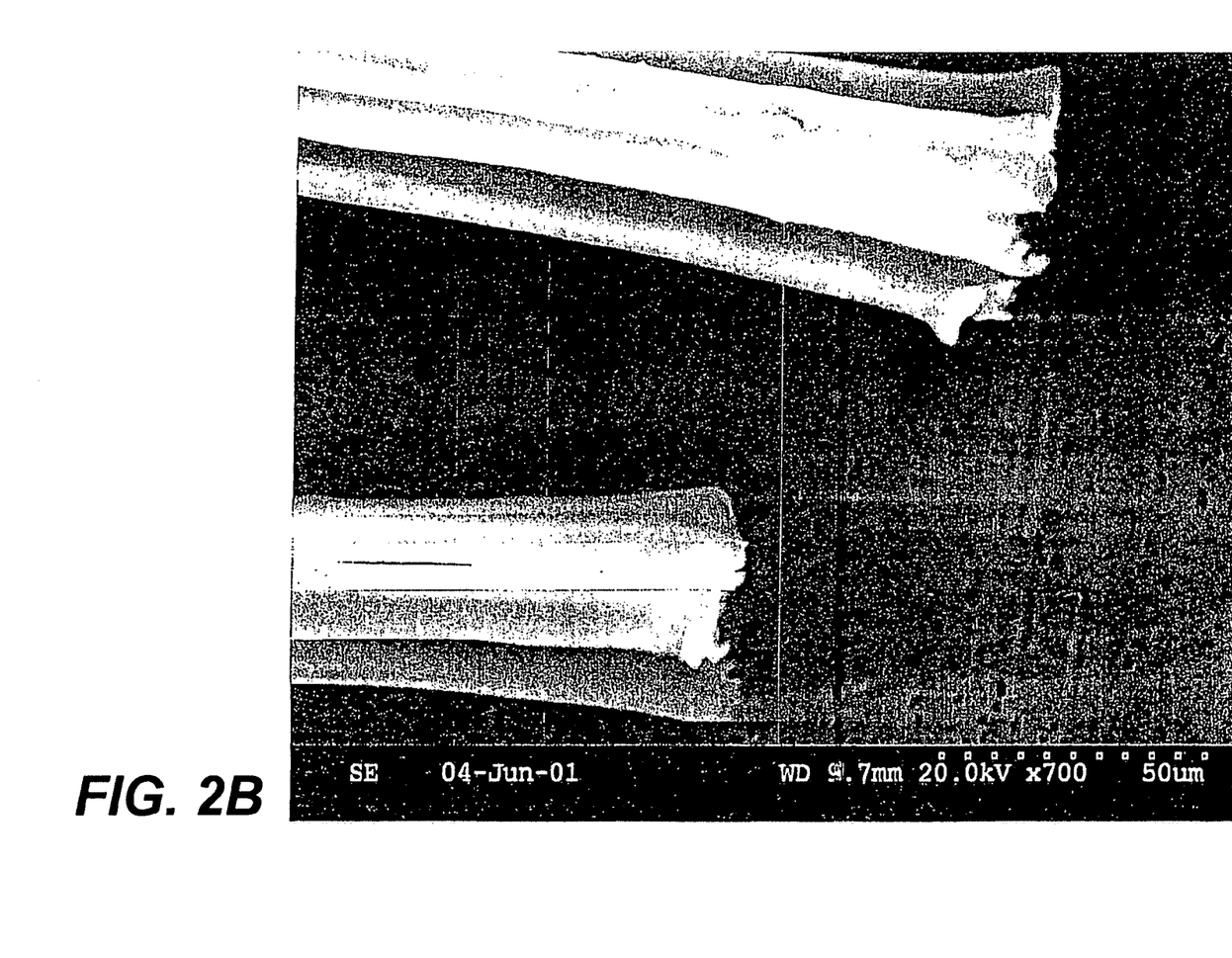
FIG. 2B is a photograph of enlarged side plan views of end portions of presently preferred embodiments of two channeled polyester fibers to be used in the column of the chromatograph.
Figure 3:
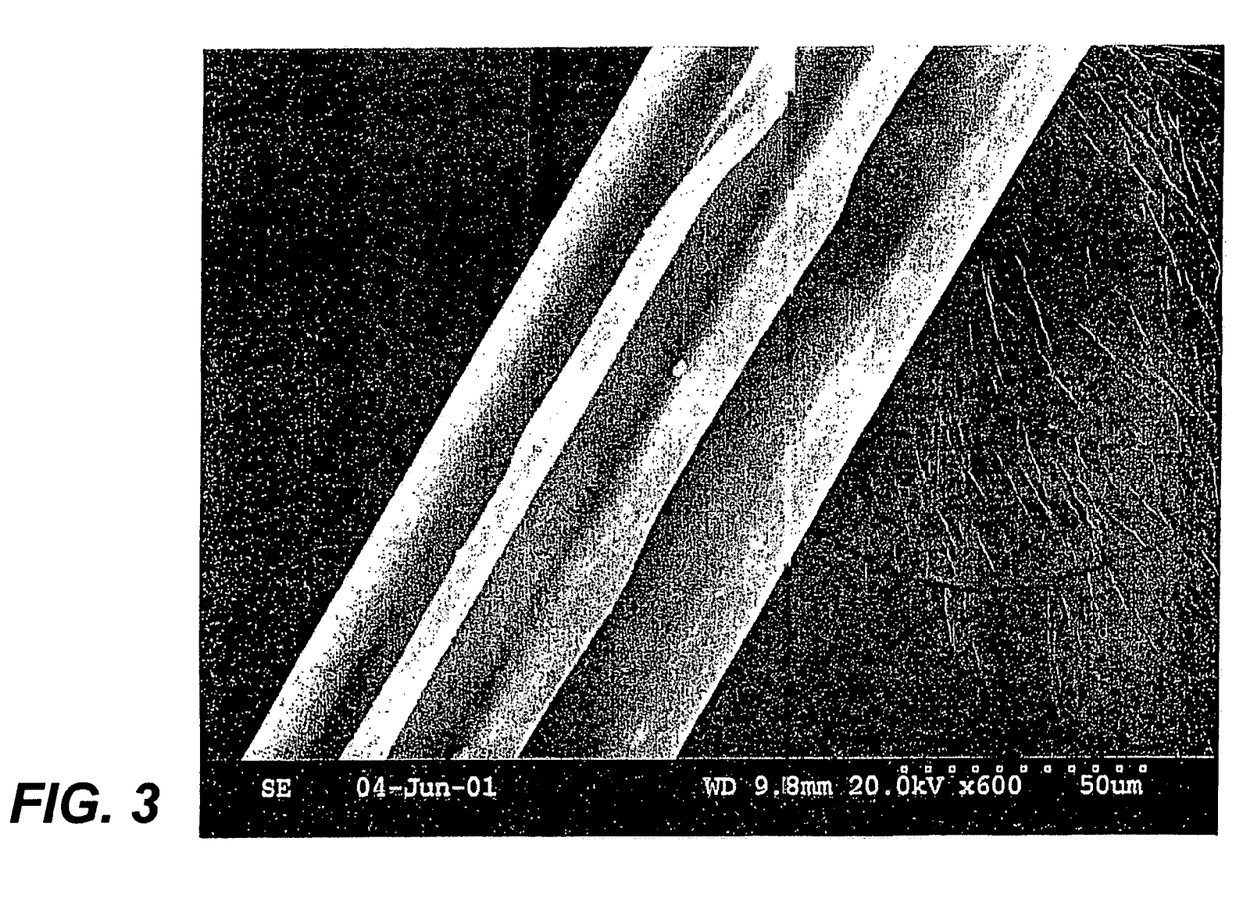
FIG. 3 is a photograph of an enlarged side plan view of an intermediate portion of a presently preferred embodiment of a channeled polypropylene fiber to be used in the column of the chromatograph.
Figure 4A:
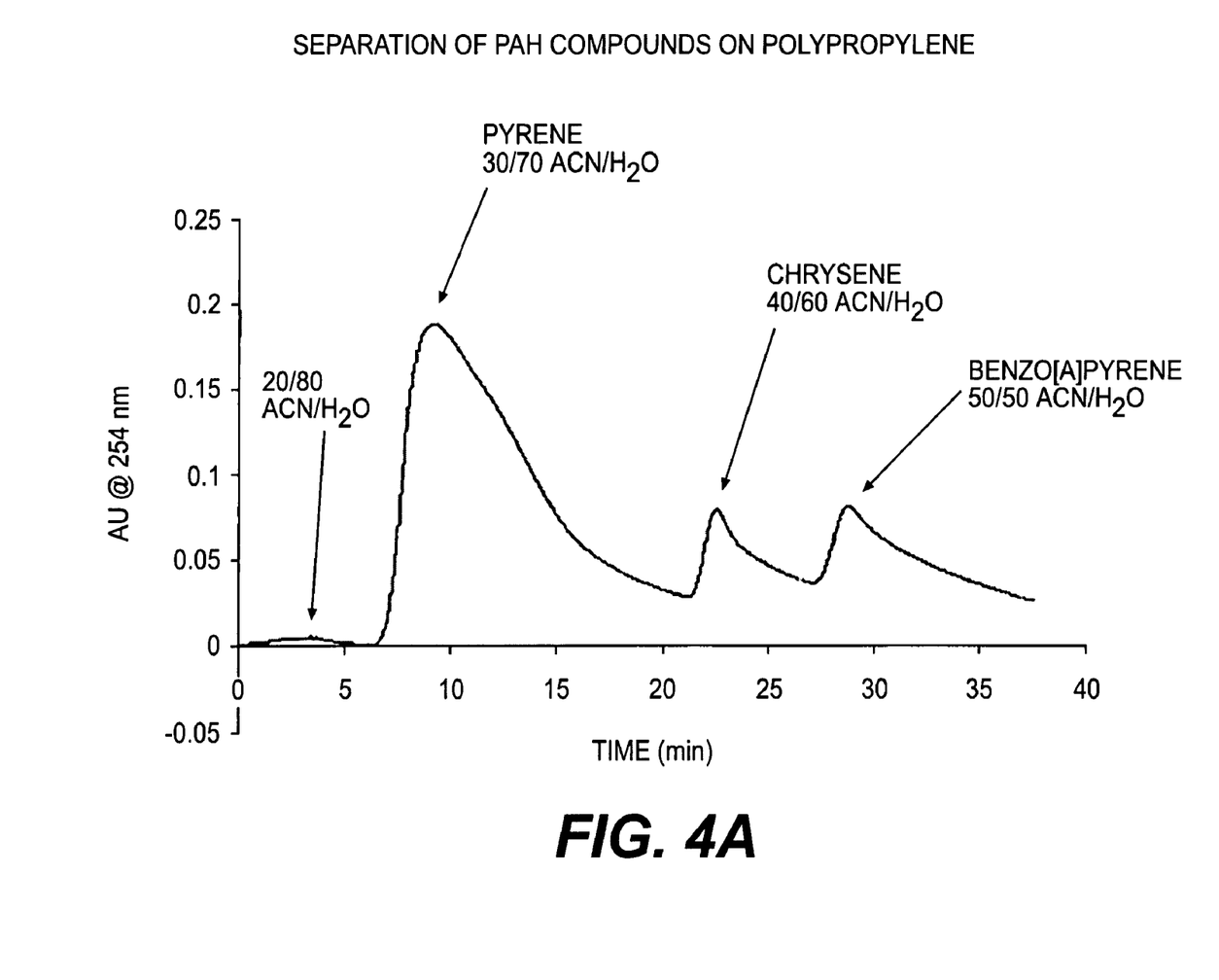
FIG. 4A is a graphical presentation of the time variation of absorbance that is illustrative of the separation of three PAH compounds by a column filled with channeled polypropylene fiber.
Figure 4B:
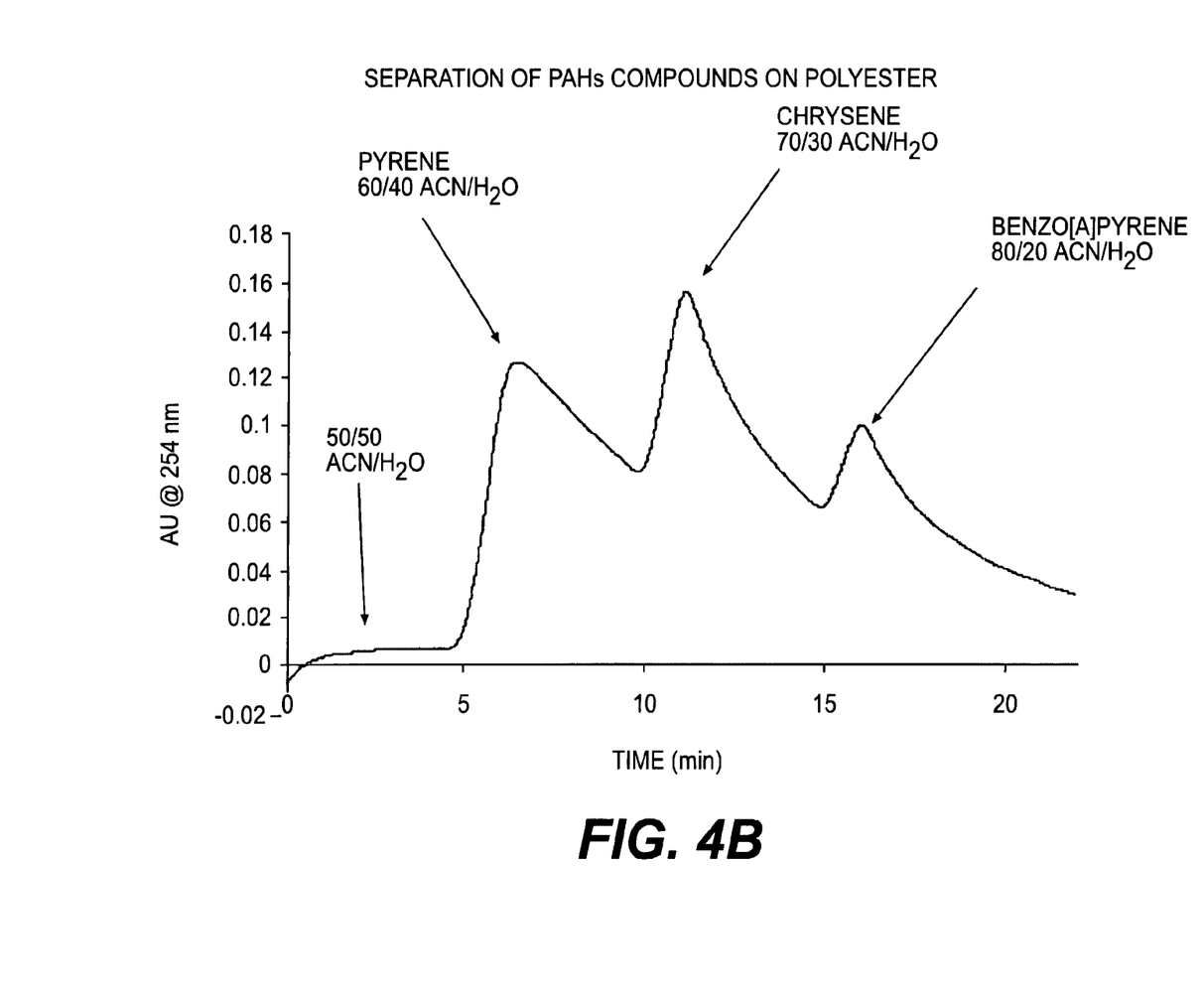
FIG. 4B is a graphical presentation of the time variation of absorbance that is illustrative of the separation of the same three PAH compounds shown in FIG. 4A, but by a column filled with channeled polyester fiber.

FIG. 4A illustrates the separation of three different PAHs on a column filled with channeled polypropylene fibers (such as shown in FIG. 3). Similarly, FIG. 4B illustrates the separation of three PAHs on a column filled with surface-channeled polyester fibers (such as shown in FIGS. 2A and 2B). As noted in FIGS. 4A and 4B, different relative concentrations of acetonitrile (ACN) to water were required to elute the solute species from the stationary phase and to obtain the chromatograms. Thus, gradient elution methods (i.e., changes in solvent composition) are required to elute the solute species from the stationary phase and to obtain the chromatograms. This is direct evidence of chemical interactions between the analyte molecules and the polymer fibers; as opposed to a more physical and mechanical "filtering" mechanism of retention of the species on the surfaces of the fibers 20.

Different from the use of channeled polymer fibers 20 for the filtration of particulate matter in liquid and vapor streams, the use of channeled fibers 20 as proposed here is clearly based on chemical interactions between the analyte/solutes and the surfaces of the polymer fibers 20. The fact that solvent gradients are required to separate the compounds as depicted in FIGS. 4A and 4B clearly demonstrates that this is the case. For example, the mixture of PAH's is completely immobilized on the polypropylene surface in aqueous solution to the point where the acetonitrile (ACN) concentration makes up 30% of the solvent composition. The same separation using polyester fibers as the stationary phase requires a 60% ACN to 40% $H_2O$ mixture; proving that the two polymers behave differently.

Liquid chromatography itself is based on the relative partitioning between the solid and solution phases, and so relative retention characteristics are an excellent indicator of the actual interactions. The use of different combinations of polymer stationary phases, analyte/solutes, and mobile phases provides empirical insights into the retention processes. In order to obtain more specific thermodynamic information about the attraction of solutes to the fibers, atomic force microscopy (AFM) can be employed to probe the surfaces. In particular, AFM probe tips having different chemical modifications (e.g., polar, hydrophobic, etc.) can be used to study the interactions. The AFM can be used to simply determine the attractive forces under different solvent conditions. However, no imaging of the surfaces is required per se.

Figure 5A:
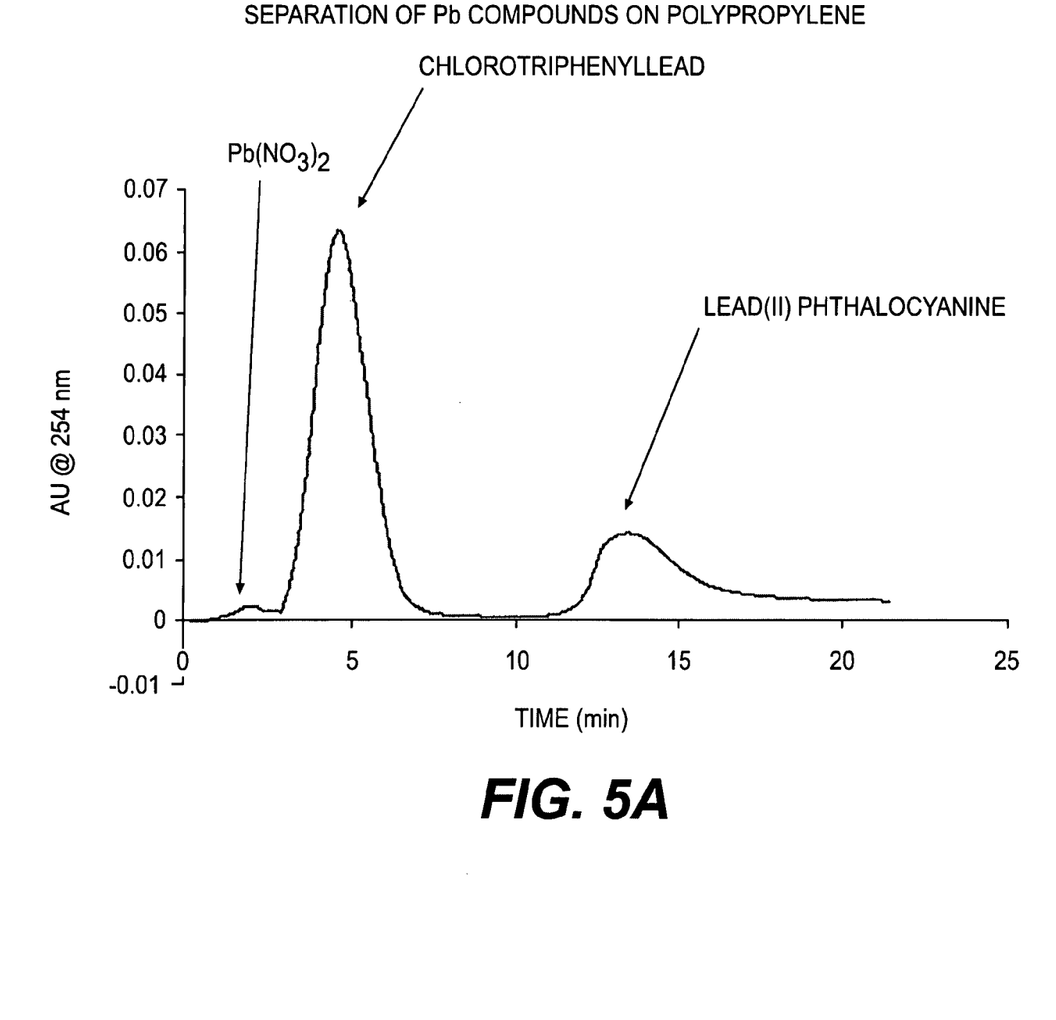
FIG. 5A is a graphical presentation of the time variation of absorbance that is illustrative of the separation of three lead-based compounds by a column filled with channeled polypropylene fiber.
Figure 5B:
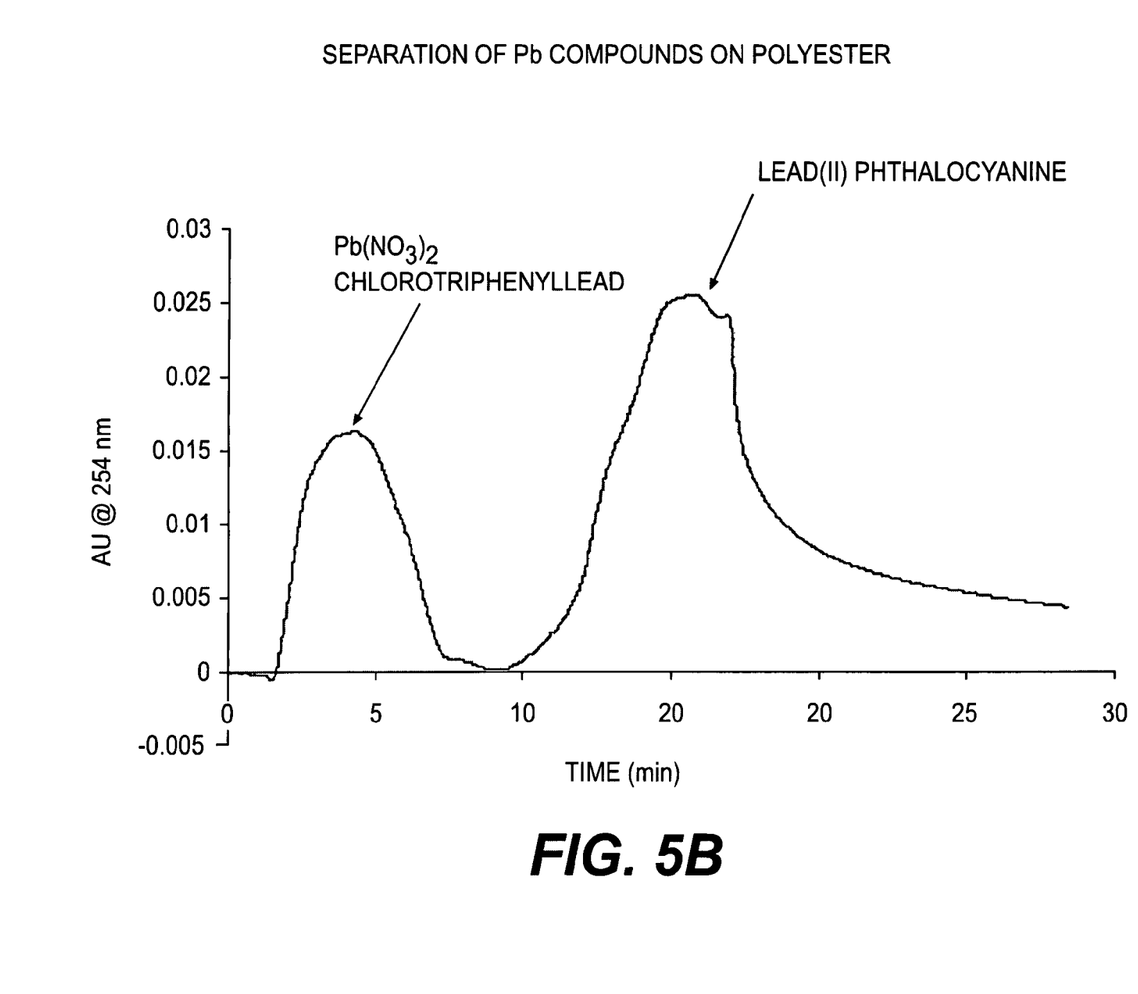
FIG. 5B is a graphical presentation of the time variation of absorbance that is illustrative of the separation of the same three lead-based compounds shown in FIG. 5A, but by a column filled with channeled polyester fiber.
Figure 6:
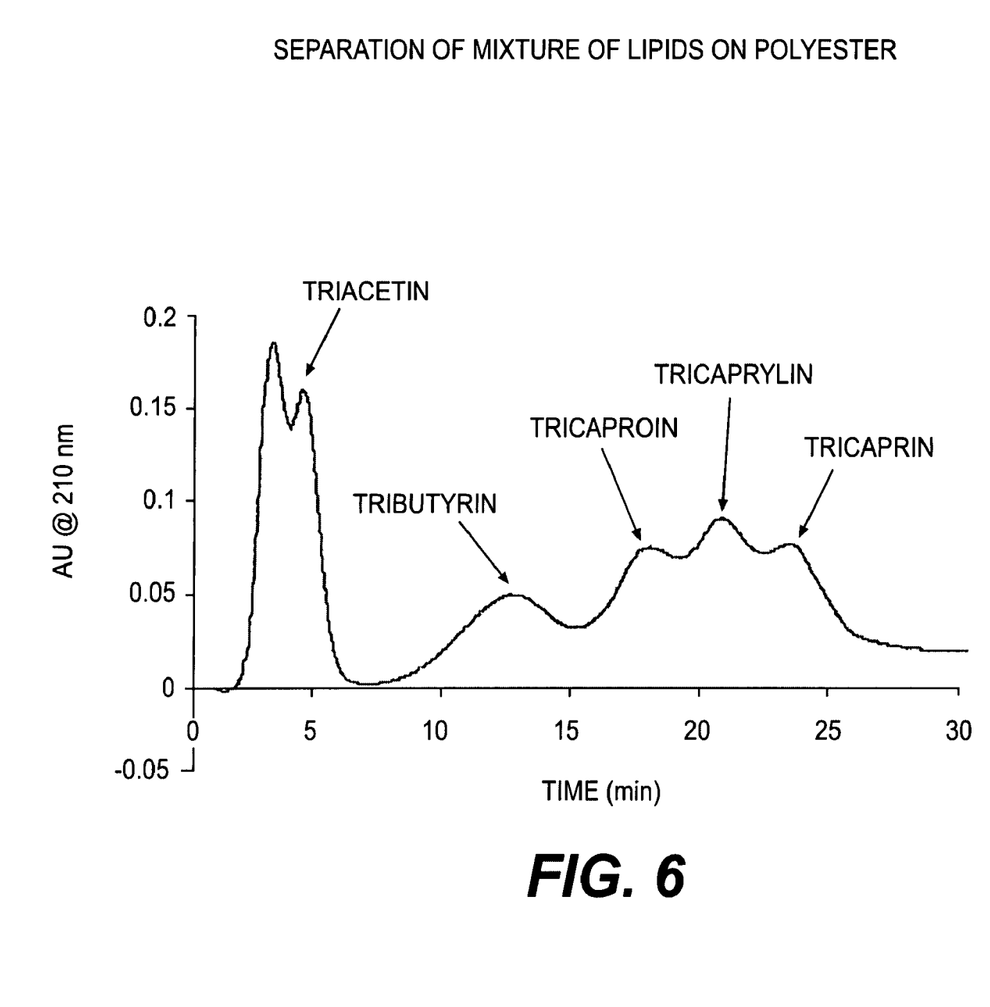
FIG. 6 is a graphical presentation of the time variation of absorbance that is illustrative of the separation of five lipid compounds by a column filled with channeled polyester fiber.

FIG. 5A illustrates the use of a column packed with channeled polypropylene fiber to separate three species of lead-based compounds. Similarly, FIG. 5B illustrates the separation of the species of these same three lead-based compounds using a column packed with channeled polyester fiber. The vertical axis in each of FIGS. 5A and 5B is a measure of the absorbance of light at 254 nanometers by each species. The greater the absorbance of that light, then the higher the number of absorbance units (AU) that is recorded on the chromatogram. The horizontal axis is the time axis that measures how long it takes for the majority of the species (the peak) to be detected by the absorbance of the light at 254 nanometers. Referring to FIG. 5A for example, the chlorotriphenyllead species shows a peak reading of about 0.06 absorbance units (AU's) of light at 254 nanometers at 5 minutes after the 0.20 milliliter volume of solution containing the chlorotriphenyllead species was introduced into the column that was packed with the channeled polypropylene fiber.

FIG. 5A illustrates that the lead nitrate species has less of a strong interaction with the polypropylene fibers in the column than either the chlorotriphenyllead species or the lead (II) phthalocyanine. The lead nitrate peak (though barely above zero) occurs earlier in time than either of the peaks of the chlorotriphenyllead species or the lead (II) phthalocyanine species. Of the three lead-based species tested, the lead nitrate species has the least affinity for the polypropylene fibers in the column. Moreover, the lead nitrate species has a different affinity for the polypropylene fibers in the column because the lead nitrate species has a different chemistry than each of the chlorotriphenyllead species and the lead (II) phthalocyanine species.

Since FIGS. 4A, 4B, 5A, 5B, 6, 7A and 7B are based on absorbance of light at a particular wavelength, the peak height of each species doesn't necessarily reflect the relative concentrations of each of the species because each of them absorbs that wavelength with different strengths.

Figure 7A:
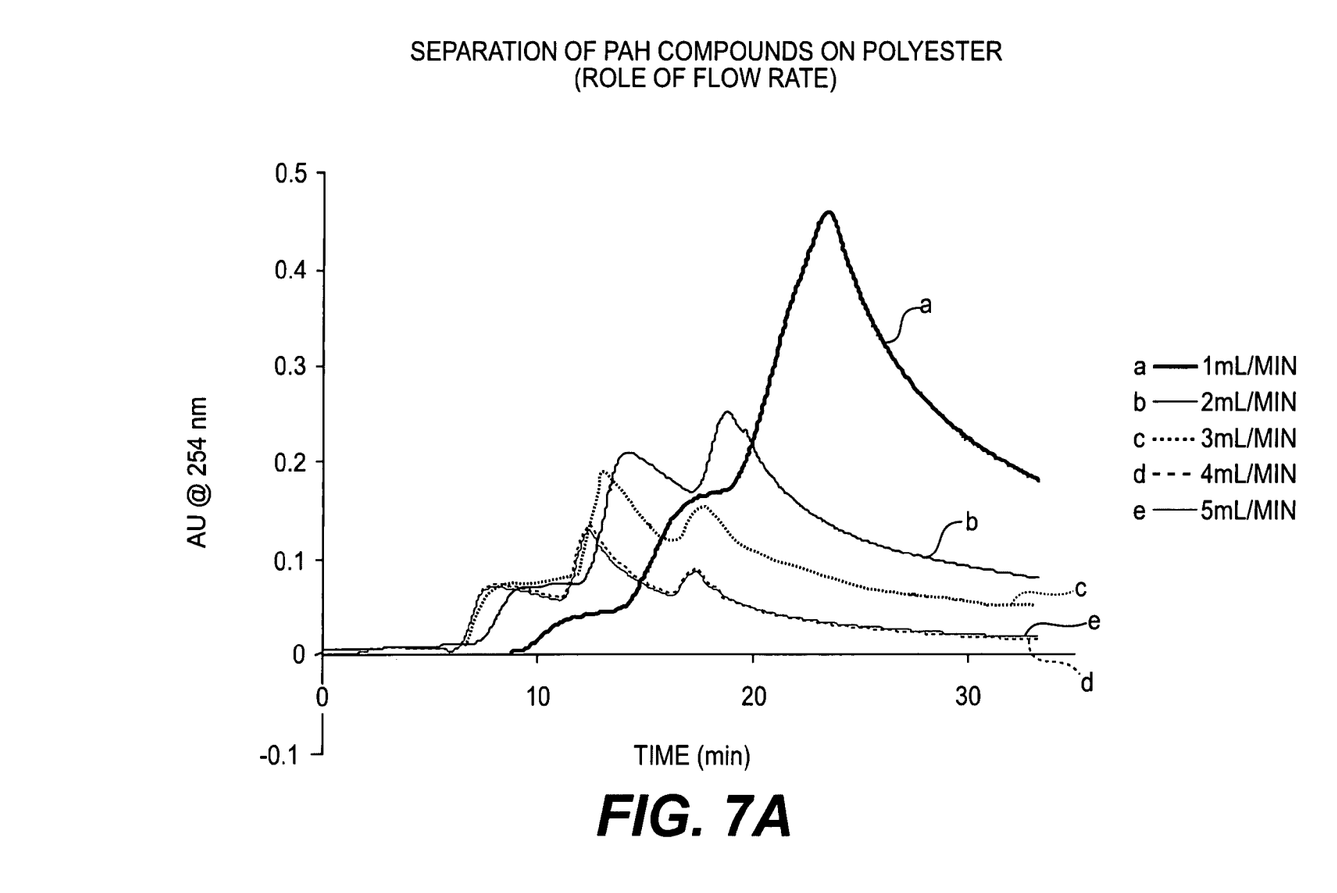
FIG. 7A is a graphical presentation of the time variation of absorbance that is illustrative of the separation of polyaromatic hydrocarbon compounds at different flow rates through a column filled with channeled polyester fiber.
Figure 7B:
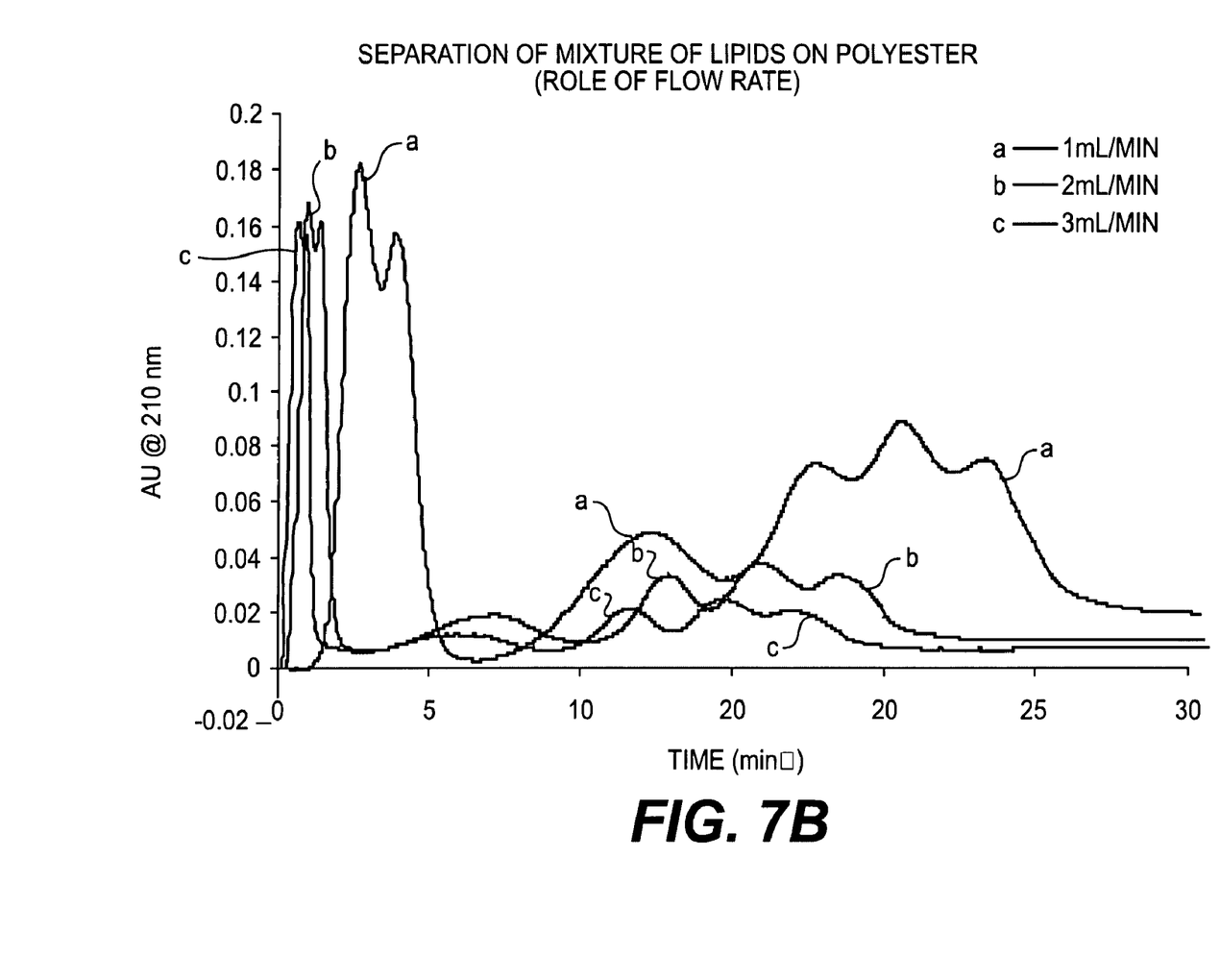
FIG. 7B is a graphical presentation of the time variation of absorbance that is illustrative of the separation of lipid compounds at different flow rates through a column filled with channeled polyester fiber.

FIGS. 7A and 7B demonstrate the role of the rate at which the volume of liquid is pumped through the column 22. In general, some of the peaks for the individual species are bigger at the low flow rates than for the high rates of flow through the column. However, the actual ability to discern one peak from another peak is as good if not better at the high rates of flow through the column than at the low flow rates. This latter finding concerning resolution of the individual peaks is counter to that observed with conventional column structures. Thus, the columns of the present invention do not exhibit degradation of the resolution of the chromatograms at the higher flow rates among those that were tested.

The surface-channeled polymer fibers 20 lend themselves to use in a variety of separation methods. A bundle composed of a plurality of surface-channeled polymer fibers 20 can be disposed with a first set of the ends of the fibers 20 inserted into a first source of a fluid containing at least one species. The second ends of the fibers 20 (the ends opposite the first ends) can be disposed at a remote location that is apart from the location of the first source of fluid. The capillary action of the channels 24 will then transport the fluid from the source to the remote location. During the course of the transport, some of the species will attach to the surfaces of the fibers 20. The species that attach to the surfaces of the fibers 20 are removed from the fluid that reaches the remote location. Accordingly, the concentration of the species at the second location becomes reduced as a result of separation of the species from the fluid by chemical attachment of the species to the surface-channeled polymer fibers 20.

A bundle composed of a plurality of surface-channeled polymer fibers 20 can be dipped into a fluid containing at least one species. Capillary action will draw a portion of the fluid Into the channels 24. During the duration of the immersion of the fibers 20 in the fluid, some of the species will attach to the surfaces of the fibers 20. The concentration of the species in the portion of the fluid that has been drawn into the channels 24 becomes reduced as a result of separation of the species from that portion of the fluid by chemical attachment of the species to the polymer fibers 20. After a predetermined duration of immersion, the fibers 20 can be withdrawn from the fluid. The species that remain attached to the surfaces of the fibers 20 are thus removed from the fluid. Accordingly, the concentration of the species that remains in the fluid becomes reduced as a result of separation of the species from the fluid by chemical attachment of the species to the surface-channeled polymer fibers 20.

It may be possible to use a single fiber in lab-on-a-chip separations.

Studies are proposed to further evaluate the potential of using channeled polymer fibers in analytical and prep-scale separations. The actual experimental procedure will involve a three-prong approach including: 1) development of column packing methodology, 2) use of atomic force microscopy to study the chemical basis of chemical specificity, and 3) investigations into on-column derivatization of the base polymer fibers.

The preliminary studies involve manual packing of the polymer fibers into the steel tubing columns 22 as depicted schematically in FIG. 1. As shown in the expanded window of FIG. 1, the present columns 22 have appreciable amounts of dead volume along the flow axis. The quality of any subsequent chemical separation is based on the uniformity of the packing of the stationary phase (fibers 20) in the column 22 with regards to dead volume, i.e., where turbulence can occur and molecule-surface interactions are absent. Therefore, a reliably reproducible way of packing the columns 22 with the channeled fibers 20 is needed before mass production of columns 22 is economically feasible.

High quality, reproducible columns 22 are required to adequately study the underlying mechanisms of retention. Desirably, radial compression technologies can be employed to effect more uniform packing of the fibers 20. For example, the steel tubing can be replaced desirably with tubing formed of polyethylene (PE), and the resulting column 22 then can be surrounded by a water jacket. Increases in pressure applied to the jacket will squeeze the polyethylene column 22 and thus compress the fibers 20 into a tighter bundle. Chemical separations of model compound classes can be performed to assess the role of compression on the retention qualities of the different fibers. Particular attention is paid to the trade-offs between packing density, the obtained resolution, and the backing pressure required to provide the desired flow through the column 22.

Another area of investigation will seek to take the basic chemical principles governing packing density and the chemical basis of chemical specificity and begin to tailor the surfaces of the polymer fibers in such a way as to have specificity for particular classes of chemical compounds. The preliminary studies have demonstrated that the polyester and polypropylene fibers have different surface chemistries, though each nominally has what is termed reverse-phase character. That is to say that each has a propensity to bind non-polar molecules. As mentioned previously, a number of other base polymers could be fabricated with these sorts of channels to gain access to other degrees of chemical specificity.

Additionally, the surfaces of the polymer fibers could be modified, while maintaining the high surface area-to-volume ratio and the basic channeled structure. Applications in analytical separations for a wide range of compound classes are anticipated by changing the identity of the base fiber or performing chemical derivatization of the surfaces of the fibers. At least portions of the channeled surfaces of the polymer fibers 20 can be modified to a predetermined chemical reactivity. For example, the predetermined chemical reactivity could be obtained by modifying at least portions of the surfaces of the surface-channeled polymer fibers 20 to a predetermined level of hydrophobicity. Thus, active sites on the fiber surfaces could be functionalized to gain more or less hydrophobic character. The predetermined chemical reactivity also could be obtained by modifying at least portions of the surfaces of the surface-channeled polymer fibers 20 to a predetermined ionic character. For example, the surfaces of fibers 20 formed from polyvinyl alcohol (PVA) might be protonated in situ by an acidic mobile phase to produce an ion exchange column.

High performance liquid chromatography will be used as the first-level screening tool in the characterization. This work will not only focus on chemical separations, but also on the capacity to retain on-column target waste species of relevance to a wide range of industries (i.e., how much solute can be immobilized in a fiber 'cartridge'?). This latter aspect is the most relevant characteristic in terms of using these fiber-types in waste stream treatment strategies.

While a preferred embodiment of the invention has been described using specific terms, such description is for illustrative purposes only, and it is to be understood that changes and variations may be made without departing from the spirit or scope of the following claims.

What is claimed is:

1. An apparatus, comprising:
   a fluid conduit having a first end and a second end disposed opposite said first end;
   a device for moving fluid through said conduit, said device being connected to said first end of said conduit;
   an instrument disposed at said second end of said conduit and configured for detecting species in a fluid moving through said conduit; and
   a plurality of polymer fibers disposed within said conduit between said first end and said second end, each said fiber being configured with a plurality of co-linear channels along the entire length of the surface of each said fiber, each said channel being defined by the opposed interior surfaces of a pair of opposed walls of said fiber, wherein at least substantial portions of the interior surfaces of the walls defining the channels of said fibers are exposed for direct contact with analyte species carried in a fluid moving through said conduit.

2. An apparatus as in claim 1, wherein each said channel of each said fiber extends helically around each said fiber.

3. An apparatus as in claim 1, wherein each said fiber is composed of polypropylene.

4. An apparatus as in claim 1, wherein a predetermined proportion by volume of said plurality of fibers is composed of a first polymer and the remaining proportion by volume of said plurality of fibers is composed of a second polymer.

5. An apparatus as in claim 4, wherein said predetermined proportion is about 50%.

6. An apparatus as in claim 1, wherein each said fiber consists essentially of polyvinyl alcohol and at least portions of said surfaces of said fiber have been protonated in situ by an acidic mobile phase.

7. An apparatus as in claim 1, wherein at least portions of said interior surfaces of said fibers have been modified to a predetermined chemical reactivity.

8. An apparatus as in claim 7, wherein said at least portions of said surfaces of said fibers have been modified to a predetermined level of hydrophobicity.

9. An apparatus as in claim 7, wherein said at least portions of said surfaces of said fibers have been modified to a predetermined ionic character.

10. An apparatus, comprising:
a fluid conduit having a first end and a second end disposed opposite said first end;
a device for moving fluid through said conduit, said device being connected to said first end of said conduit;
an instrument disposed at said second end of said conduit and configured for detecting species in a fluid moving through said conduit; and
a single polymer fiber disposed within said conduit between said first end and said second end, said fiber being configured with a plurality of co-linear channels along the entire length of the surface of said fiber, each said channel being defined by the opposed interior surfaces of a pair of opposed walls of said fiber, wherein at least substantial portions of said interior surfaces of the walls defining the channels of said fiber are exposed for direct contact with analyte species carried in a fluid moving through said conduit.

11. An apparatus, comprising:
a fluid conduit having a first end and a second end disposed opposite said first end;
a device for moving fluid through said conduit, said device being connected to said first end of said conduit; and
a plurality of polymer fibers disposed within said conduit between said first end and said second end, each said fiber being configured with a plurality of co-linear channels along the entire length of the surface of each said fiber, each said channel being defined by the opposed interior surfaces of a pair of opposed walls of said fiber, wherein at least substantial portions of said interior surfaces of the walls defining the channels of said fibers are exposed for direct contact with analyte species carried in a fluid moving through said conduit.

* * * * *